United States Patent
Yoh et al.

(10) Patent No.: US 11,369,741 B2
(45) Date of Patent: Jun. 28, 2022

(54) AUTOMATIC RECHARGING MICRO-JET DRUG INJECTION DEVICE PREVENTING JET SPEED DOWN PROBLEM OF REPEATED INJECTION

(71) Applicant: SNU R&DB FOUNDATION, Seoul (KR)

(72) Inventors: Jai-Ick Yoh, Seoul (KR); Hwi-Chan Ham, Seoul (KR); Hun Jae Jang, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 1043 days.

(21) Appl. No.: 15/824,423

(22) Filed: Nov. 28, 2017

(65) Prior Publication Data

US 2018/0154082 A1    Jun. 7, 2018

(30) Foreign Application Priority Data

Nov. 3, 2016    (KR) .................. 10-2016-0145666

(51) Int. Cl.
*A61M 5/30*    (2006.01)
*A61M 5/48*    (2006.01)
(Continued)

(52) U.S. Cl.
CPC ............ *A61M 5/30* (2013.01); *A61M 5/1782* (2013.01); *A61M 5/2046* (2013.01); *A61M 5/482* (2013.01); *A61B 2018/263* (2013.01)

(58) Field of Classification Search
CPC .... A61M 5/30; A61M 5/1782; A61M 5/2046; A61M 5/482; A61M 5/20; A61M 5/31; A61B 2018/263
See application file for complete search history.

(56) References Cited

U.S. PATENT DOCUMENTS 2,821,981 A * 2/1958 Kish ................. A61M 5/30
604/71
3,057,349 A * 10/1962 Ismach ................ A61D 7/00
604/71
(Continued)

FOREIGN PATENT DOCUMENTS

GB    191402491 A * 8/1914
KR    20070018726    2/2007
(Continued)

OTHER PUBLICATIONS

Han, et al., A laser based reusable microjet injector for transdermal drug delivery, Journal of Applied Physics, 2010.
(Continued)

*Primary Examiner* — Nathan R Price
*Assistant Examiner* — Mark A Igel
(74) *Attorney, Agent, or Firm* — STIP Law Group, LLC

(57) ABSTRACT

Provided is a micro-jet drug injection device comprising: a pressure chamber having a pressure driving liquid hermetically filled therein; a drug chamber having a micro nozzle defined in a wall; an elastic membrane elastically expandable and restorable and to separate the pressure chamber from the drug chamber; an energy-focusing unit concentrating energy on the pressure driving liquid in the pressure chamber; and the storage unit supplying the drug solution therein into the drug chamber through a drug supply channel. The drug chamber has a partial inner space defined therein. The partial inner space is in fluid communication with the drug supply channel and is partially defined by the membrane. A nozzle closure is disposed inside or outside the drug chamber. The nozzle closure blocks inflow of air outside the micro-nozzle into the partial inner space after the elastic membrane has expanded and before elastic recovery of the membrane is completed.

16 Claims, 6 Drawing Sheets

(51) Int. Cl.
*A61M 5/20* (2006.01)
*A61M 5/178* (2006.01)
*A61B 18/26* (2006.01)

(56) References Cited

U.S. PATENT DOCUMENTS

| | | | | |
|---|---|---|---|---|
| 3,130,723 | A * | 4/1964 | Venditty | A61M 5/30 |
| | | | | 604/71 |
| 3,805,783 | A * | 4/1974 | Ismach | A61M 5/30 |
| | | | | 604/71 |
| 4,059,107 | A * | 11/1977 | Iriguchi | A61M 5/30 |
| | | | | 604/71 |
| 4,135,866 | A | 1/1979 | Winkler | |
| 4,342,310 | A * | 8/1982 | Lindmayer | A61M 5/30 |
| | | | | 604/71 |
| 4,403,986 | A * | 9/1983 | Dettbarn | A61M 5/30 |
| | | | | 604/70 |
| 5,024,656 | A * | 6/1991 | Gasaway | A61M 5/30 |
| | | | | 604/141 |
| 5,406,889 | A | 4/1995 | Letendre et al. | |
| 5,599,302 | A * | 2/1997 | Lilley | F41B 11/642 |
| | | | | 604/500 |
| 5,713,845 | A | 2/1998 | Tankovich | |
| 5,725,493 | A * | 3/1998 | Avery | A61F 9/0017 |
| | | | | 604/9 |
| 5,741,247 | A | 4/1998 | Rizoiu et al. | |
| 6,086,580 | A * | 7/2000 | Mordon | A61N 5/062 |
| | | | | 606/9 |
| 6,641,553 | B1 * | 11/2003 | Chee | A61B 17/32037 |
| | | | | 604/68 |
| 7,400,940 | B2 * | 7/2008 | McRae | A61M 11/041 |
| | | | | 700/282 |
| 7,449,009 | B2 * | 11/2008 | Eichhorst | A61M 5/204 |
| | | | | 604/70 |
| 8,905,966 | B2 | 12/2014 | Yoh et al. | |
| 9,067,019 | B2 * | 6/2015 | Menassa | A61M 5/30 |
| 10,507,287 | B2 * | 12/2019 | Jeon | A61M 5/282 |
| 2002/0045911 | A1 | 4/2002 | Fletcher | A61B 17/3203 |
| | | | | 606/167 |
| 2002/0177772 | A1 * | 11/2002 | Altman | B82Y 5/00 |
| | | | | 600/431 |
| 2003/0014014 | A1 * | 1/2003 | Nitzan | A61M 5/14216 |
| | | | | 604/158 |
| 2003/0114789 | A1 * | 6/2003 | Haar | A61M 5/30 |
| | | | | 604/69 |
| 2003/0139041 | A1 | 7/2003 | Leclair | |
| 2004/0260234 | A1 * | 12/2004 | Srinivasan | A61M 15/008 |
| | | | | 604/890.1 |
| 2007/0049873 | A1 * | 3/2007 | Hansen | A61M 5/2425 |
| | | | | 604/187 |
| 2007/0069131 | A1 | 3/2007 | Banerjee et al. | |
| 2007/0233019 | A1 * | 10/2007 | Forsell | A61M 5/172 |
| | | | | 604/288.03 |
| 2009/0129945 | A1 * | 5/2009 | Adleff | A61K 9/0004 |
| | | | | 204/600 |
| 2011/0230826 | A1 * | 9/2011 | Yoh | A61M 5/30 |
| | | | | 604/70 |
| 2013/0066263 | A1 * | 3/2013 | Yoh | A61M 5/30 |
| | | | | 604/70 |
| 2015/0265770 | A1 * | 9/2015 | Yoh | A61M 5/31 |
| | | | | 604/70 |
| 2018/0154082 | A1 * | 6/2018 | Yoh | A61M 5/1782 |
| 2019/0255253 | A1 * | 8/2019 | Yoh | A61M 5/2053 |
| 2019/0321568 | A1 * | 10/2019 | Stedman | A61M 15/0035 |

FOREIGN PATENT DOCUMENTS

| | | | |
|---|---|---|---|
| KR | 20110104409 | | 9/2011 |
| KR | 20120105718 | A * | 9/2012 |
| KR | 20140140739 | | 12/2014 |
| KR | 20140140747 | A * | 12/2014 |
| KR | 101684250 | B1 * | 12/2016 |
| KR | 20120105718 | A * | 9/2021 |
| WO | 2010047825 | | 4/2010 |
| WO | WO-2011115422 | A2 * | 9/2011 ............. A61M 5/30 |
| WO | WO-2014025241 | A1 * | 2/2014 ............. A61M 35/00 |

OTHER PUBLICATIONS

Lee, et al., Skin pretreatment with an Er.YAG laser promotes the transdermal delivery of three narcotic analgesics, Lasers Med Sci, 2007, pp. 271-278.

Menezes, et al., Shock wave driven liquid microjets for drug delivery, Journal of Applied Physics, 2009.

Sankin, et al., Interaction between shock wave and single inertial bubbles near an elastic boundary, Phys Rev E Stat Nonlin Soft Matter Phys, 2006, pp. 1-10.

Stachowiak, et al., Dynamic control of needle-free jet injection, Journal of Controlled Release, 2009, pp. 104-112.

* cited by examiner

AUTOMATIC RECHARGING MICRO-JET DRUG INJECTION DEVICE PREVENTING JET SPEED DOWN PROBLEM OF REPEATED INJECTION

BACKGROUND

Field of the Present Disclosure

The present disclosure relates to a microjet drug injection device that ejects an injected drug in a high-speed microjet form to penetrate the drug microjet into a target portion. More particularly, the present disclosure relates to an improved microjet drug injection device configured to prevent an ejection rate and penetration performance from being degraded due to creation of air bubbles in a drug solution contained within an injector after the microjet ejection.

Discussion of Related Art

In general, a variety of drug delivery systems have been applied as a method for parenterally administering a treatment drug solution into a patient's body in a medical field. In these drug delivery systems, the most commonly used method is a method using a needle-type syringe. In this method, a syringe having a syringe needle is pierced into a patient's skin, and a drug solution is directly injected. The conventional needle-type syringe as described above is advantageously simple in structure, easy to use, and has a merit that substantially quantitative drug injection is enabled because a piston-type injection port is used. However, such a conventional needle-type injection method has a great shortcoming in that the patient suffers from an inconvenience of feeling a pain during the injection. In addition, the injection method has many problems such as a wound caused by perforation of a skin layer, a risk of secondary infection through the wound, and waste of resources due to difficulty in reusing the syringe.

Due to the shortcomings of the conventional needle-type syringe, development of needle-free drug delivery systems as a substitute for the needle-type syringe has been widely researched. In an attempt to develop the needle-free drug delivery system, there has been proposed a drug delivery system of ejecting a drug solution in a form of a microjet having a micro diameter at a high speed and allowing the drug solution to be directly penetrated into an internal target spot through epidermis.

In the microjet drug delivery system, in order to produce a high-speed drug microjet, a strong propulsion force is applied (directly or indirectly) onto the ejected drug, so that the drug is forced out externally through a micro-nozzle orifice. In this microjet drug delivery system, the propulsion force generation approach has been variously developed since 1930s. Various ejection methods have been developed as follows. Until recently, piezoelectric ceramics were used for ejection. Alternatively, an ejection method using a shock wave induced by applying a laser beam to an aluminum foil, a method using a compression spring or a compressed gas, or an ejection method using Lorentz force has been employed.

In recent years, unlike the conventional microjet ejection methods, a laser-bubble type microjet ejection has been developed by the present applicant. In this laser-bubble type microjet ejection, the amount of ejected drug and the ejection rate (i.e. drug penetration depth) may be finely adjusted, and continuous injection and reusability may be achieved.

This laser-bubble type technique has been filed as Korean Patent Application No. 10-2010-56637 (titled "microjet drug delivery system"). The above patent application is patented as KR registration number 1207977.

FIG. 10 shows a laser-bubble type microjet drug delivery device as described in the above-mentioned patent document. FIG. 10a shows a state before the ejection of the drug, and FIG. 10b shows a state where the drug is ejected. Referring to FIG. 10, the microjet drug delivery device described in the above patent document includes a pressure chamber 10 having a pressure driving liquid hermetically filled therein, a drug chamber 20 disposed adjacent to the pressure chamber 10 to store a drug solution therein, an elastic membrane 30 disposed between the pressure chamber 10 and the drug chamber 20 to partition the pressure chamber and the drug chamber, and an energy focusing unit 40 configured to apply strong energy of a laser beam or the like onto an inner portion of the pressure chamber 10 to change the pressure driving liquid from a gas state to a liquid state.

According to the above-described microjet drug delivery device as described in the above patent document, when the energy focusing unit 40 irradiates the pressure driving liquid 100 into the pressure chamber 10 with the strong energy of the laser beam or the like in a concentrated manner, the pressure driving liquid 100 evaporates momentarily, thus, a bubble is generated therein. Then, during rapid expansion and disappearance of the generated bubble, the elastic membrane 30 is expanded. Due to the expansion of the elastic membrane, the drug solution in the drug chamber 20 is rapidly pressured and ejected through the nozzle, so that the microjet of the drug solution is injected at an enough speed to penetrate soft tissue of the body.

However, in the microjet drug delivery device as disclosed in the above patent document, after drug microjet ejection, unintended and unnecessary bubbles are created in the drug chamber 20 containing the drug liquid therein. Due to the growth of the bubble, the pressure resulting from the expansion deformation of the elastic membrane is not transferred to the drug solution. As a result, microjet ejection characteristics and efficiency are lowered, and as a result, the penetration performance is greatly deteriorated.

Particularly, in the case of using a laser device as an energy source in a microjet drug delivery device as disclosed in the above patent document, by continuously ejecting a small amount of drug using a laser oscillating at several times (more than 10 times) per second, the dose of the injected drug is adjusted as necessary. However, as the number of ejections increases in such continuous ejection, the bubble in the drug chamber grows. After many repetitive ejections, a problem has been found that the device becomes unusable. The present applicant found from the test result that the jet speed of the conventional microjet drug delivery device is 140 m/s at an initial stage, decreases to 60 m/s after 200 shots, and then to 20 m/s after 600 shots.

The bubble generation in the drug chamber after the ejection is predicted to be caused by the external air inflow due to the decrease of the internal pressure of the drug chamber immediately after the ejection. That is, due to the vapor bubble 120 generated in the pressure-driving liquid 100 in the pressure chamber 10 during microjet ejection, the elastic membrane is initially expanded in the direction to pressurize the drug solution, but, the bubble 120 disappears, so that the pressure in the drug chamber becomes lower than the atmospheric pressure during the recovery of the elastic membrane 30 to its original position. Thus, due to the pressure difference between the internal pressure of the drug chamber and the external atmospheric pressure, back-pressure is generated and thus air flows into the drug chamber from the outside of the nozzle.

At this time, the air introduced into the drug chamber floats upward due to the specific gravity difference with the drug solution and air, and then occupies a location beneath the elastic membrane 30. The air bubble gradually grows beneath the elastic membrane due to air entering the chamber each time the ejection is repeated (the air enters the chamber at the same volume as the ejected drug). This leads to a significant reduction in the pressure delivered from the elastic membrane to the drug liquid during subsequent ejection. As a result, the ejection characteristics of the microjet and the penetration performance of the skin of the microjet are deteriorated.

Therefore, the present applicant discloses a method to solve the ejection efficiency deterioration due to the air bubble generation in the drug chamber after microjet ejection. In this method, before back-pressure occurs after microjet ejection, the operation of a drug supply device connected to the injector is controlled to supply the same amount of drug as the amount of previously ejected drug into the drug chamber in a timely manner. As a result, it is possible to suppress the inflow of external air into the drug chamber by the back-pressure and to suppress the generation of bubbles in the drug chamber. This method was filed as Korean Patent Application No. 10-2013-0061485 (titled "method to control drug supply in microjet drug delivery device, and microjet drug delivery system using the method). The above patent application was patented as Korean Patent No. 10-1500568.

However, according to the method of controlling the drug supply in the microjet drug delivery device as disclosed in the patent document, in order to achieve the above effect, the drug supply device and the laser device should be controlled so that the timings of driving the drug supply device and the laser device are accurately correlated with each other. However, in practical implementation, the control of these devices is very difficult, and therefore the desired effect has not been achieved satisfactorily. That is, according to the method as disclosed in the above patent document, an appropriate effect will be achieved only by supplying the exact amount of drug from the exact time point at which the internal pressure is reduced due to the disappearance of the bubble generated in the pressure chamber after ejection of the microjet. Actually, however, the behavior of the bubble inside the pressure driving liquid, and the elastic membrane, and thus the internal pressure change may vary depending on the type of drug, and environmental conditions such as the ambient temperature, and the condition of use. Therefore, it has been difficult to achieve the expected effect as described above.

Further, according to the method described in the above patent document, the operation of the drug supply device must be synchronized with the operation of the laser device. Thus, when a microjet injector unit is mounted on a conventional laser device, simply attaching the injector to the laser tip may not suffice. Therefore, additional technical measures are needed. As a result, in the construction of the drug supply device, there is a disadvantage in terms of the structure of the device, since driving means such as a micro pump (piezoelectric drive, pneumatic drive, etc.) must be additionally provided to supply the drug.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

The present disclosure has been made in order to solve the problems in the above-described microjet ejection type drug injector. The present disclosure provides a microjet drug injection device that ejects an injected drug in a high-speed microjet form to penetrate the drug microjet into a target portion, whereby after the ejection of the drug solution, unwanted air bubbles are prevented from being created in the drug chamber where the drug is stored, and, thus, degradation of ejection characteristics and efficiency due to bubble creation in the drug chamber after microjet drug ejection is suppressed, and even with many repetitive ejections, constant speed and penetration performance is maintained irrespective of the number of ejection times.

Further, the present disclosure provides a microjet drug injection device whereby, without the need for additional precise control devices or complicated mechanical mechanisms, the amount of the drug solution equal to the amount of the drug ejected each time is automatically refilled into the chamber, thereby enabling automatic refilling with a simple configuration.

In a first aspect of the present disclosure, there is provided a microjet drug injection device comprising: a pressure chamber having a sealed inner space defined therein, wherein a pressure driving liquid is hermetically filled in the pressure chamber; a drug chamber having a drug solution contained therein, wherein the drug chamber has a micro nozzle defined in a wall thereof for discharging the drug solution out of the drug chamber; an elastic membrane configured to be elastically expandable and restorable and to separate the pressure chamber and the drug chamber from each other; an energy-focusing unit configured to concentrates energy on the pressure driving liquid in the pressure chamber to create a bubble in the pressure chamber; a drug storage unit being in fluid communication with the drug chamber through a drug supply channel, wherein the drug storage unit contains a drug solution stored therein, and the storage unit is configured to supply the drug solution into the drug chamber through the drug supply channel, wherein the drug chamber has a partial inner space defined therein, wherein the partial inner space is in fluid communication with the drug supply channel and is partially defined by the membrane; and a nozzle closure disposed inside or outside the drug chamber, wherein the nozzle closure is configured to block inflow of air outside the micro-nozzle into the partial inner space after the elastic membrane has expanded and before elastic recovery of the membrane is completed.

In one embodiment of the first aspect, the nozzle closure is disposed inside the drug chamber, wherein the drug chamber is partitioned into a first inner space and a second inner space by an intermediate wall, and the first space and the second space are in fluid communication through an opening defined in the intermediate wall, wherein the nozzle is defined in the wall defining the second space, wherein the partial inner space corresponds to the first space.

In one embodiment of the first aspect, the nozzle closure includes a check valve, wherein the check valve is configured to allow movement of the drug solution from the first space to the second space, but to block movement of the drug solution from the second space to the first space.

In one embodiment of the first aspect, the nozzle closure includes: a bearing ball having a diameter greater than the opening; and a support spring configured for elastically supporting the bearing ball such that the bearing ball closes the opening.

In one embodiment of the first aspect, when an inner pressure of the first space drops due to ejection of the drug solution from the first space out of the drug chamber, the drug solution is sucked from the storage unit into the first space by a pressure difference between the first space and an inner space of the storage unit.

In one embodiment of the first aspect, the energy-focusing unit includes a laser unit configured to irradiate a laser beam to the pressure driving liquid in the pressure chamber.

In one embodiment of the first aspect, the laser beam emitted from the laser unit is focused at one point in the pressure driving liquid.

In one embodiment of the first aspect, the laser unit include an Er:YAG laser unit.

In a second aspect of the present disclosure, there is provided a microjet drug injection device comprising: a pressure chamber having a sealed inner space defined therein, wherein a pressure driving liquid is hermetically filled in the pressure chamber; a drug chamber having a drug solution contained therein, wherein the drug chamber has a micro nozzle defined in a wall thereof for discharging the drug solution out of the drug chamber, wherein the drug chamber fluid-communicates with an external drug supply channel, wherein the drug chamber is partitioned into a first inner space and a second inner space by an intermediate wall, and the first space and the second space are in fluid communication through an opening defined in the intermediate wall, wherein the nozzle is defined in the wall defining the second space, wherein the drug supply channel fluid-communicates with the first space; an elastic membrane configured to be elastically expandable and restorable and to separate the pressure chamber and the drug chamber from each other, wherein the first space is partially defined by the membrane; an energy-focusing unit configured to concentrates energy on the pressure driving liquid in the pressure chamber to create a bubble in the pressure chamber; and a nozzle closure disposed in the second space, wherein the nozzle closure includes a check valve, wherein the check valve is configured to allow movement of the drug solution from the first space through the opening to the second space, but to block movement of the drug solution from the second space to the first space.

In one embodiment of the second aspect, the nozzle closure includes: a bearing ball having a diameter greater than the opening; and a support spring configured for elastically supporting the bearing ball such that the bearing ball closes the opening.

In a third aspect of the present disclosure, there is provided a microjet drug injection device, wherein the device is removably mounted to a laser tip of a laser unit to emit a laser beam, wherein the device comprises: a pressure chamber having a sealed inner space defined therein, wherein a pressure driving liquid is hermetically filled in the pressure chamber, wherein when the laser unit is mounted to the laser tip and the laser beam is irradiated into the pressure driving liquid in the pressure chamber to create a bubble in the pressure chamber; a drug chamber having a drug solution contained therein, wherein the drug chamber has a micro nozzle defined in a wall thereof for discharging the drug solution out of the drug chamber; an elastic membrane configured to be elastically expandable and restorable and to separate the pressure chamber and the drug chamber from each other; a drug storage unit being in fluid communication with the drug chamber through a drug supply channel, wherein the drug storage unit contains a drug solution stored therein, and the storage unit is configured to supply the drug solution into the drug chamber through the drug supply channel, wherein the drug chamber has a partial inner space defined therein, wherein the partial inner space is in fluid communication with the drug supply channel and is partially defined by the membrane; and a nozzle closure disposed inside or outside the drug chamber, wherein the nozzle closure is configured to block inflow of air outside the micro-nozzle into the partial inner space after the elastic membrane has expanded and before elastic recovery of the membrane is completed.

In one embodiment of the third aspect, the nozzle closure is disposed inside the drug chamber, wherein the drug chamber is partitioned into a first inner space and a second inner space by an intermediate wall, and the first space and the second space are in fluid communication through an opening defined in the intermediate wall, wherein the nozzle is defined in the wall defining the second space, wherein the partial inner space corresponds to the first space.

In one embodiment of the third aspect, the nozzle closure includes a check valve, wherein the check valve is configured to allow movement of the drug solution from the first space to the second space, but to block movement of the drug solution from the second space to the first space.

In one embodiment of the second aspect, the nozzle closure includes: a bearing ball having a diameter greater than the opening; and a support spring configured for elastically supporting the bearing ball such that the bearing ball closes the opening.

In the microjet drug injection device according to the present disclosure, after ejection of the drug solution, external air is prevented from being introduced into the drug chamber and, thus, unintended air bubbles are prevented from being created. This may prevent deterioration of ejection characteristics and efficiency due to bubble generation in the drug chamber after microjet drug ejection. Accordingly, even in the case of continuous ejections of many repetitions, regardless of the number of ejections, a constant ejection rate, ejection volume, and skin penetration performance may be maintained.

Further, in the microjet drug injection device according to the present disclosure, without the need for additional precise control devices or complicated mechanical mechanisms, the amount of the drug solution equal to the amount of the drug ejected each time is automatically refilled into the chamber, thereby enabling automatic refilling with a simple configuration.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTIONS

Figure 1:
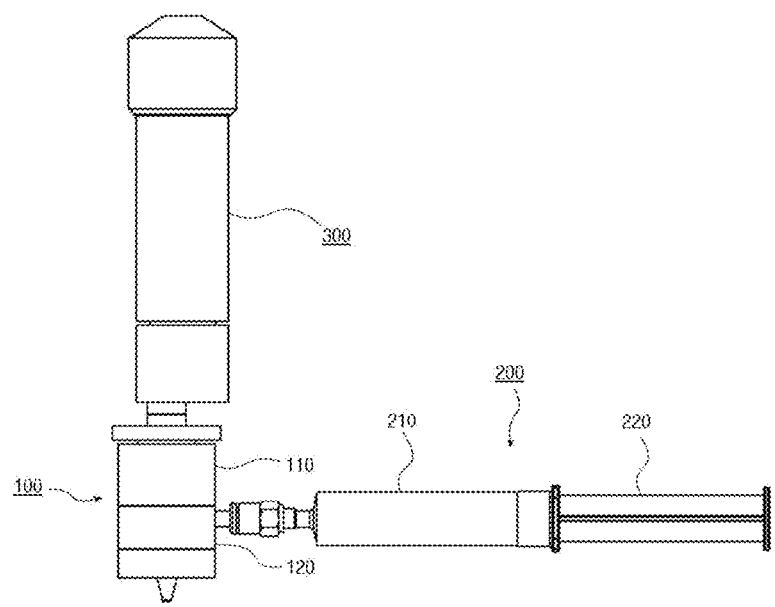
FIG. 1 is a diagram showing an overall configuration of a microjet drug injection device according to the present disclosure.

For simplicity and clarity of illustration, elements in the figures are not necessarily drawn to scale. The same reference numbers in different figures denote the same or similar elements, and as such perform similar functionality. Also, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented for example, rotated 90 degrees or at other orientations, and the spatially relative descriptors used herein should be interpreted accordingly.

The terminology used herein is for the purpose of describing particular embodiments only and is not intended to be limiting of the present disclosure. As used herein, the singular forms "a" and "an" are intended to include the plural forms as well, unless the context dearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

Figure 2:
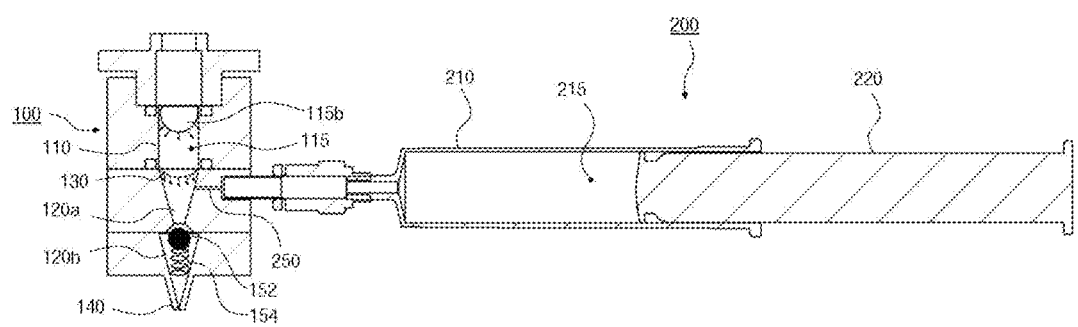
FIG. 2 is a view showing a cross-sectional structure of the device shown in FIG. 1.
Figure 3:
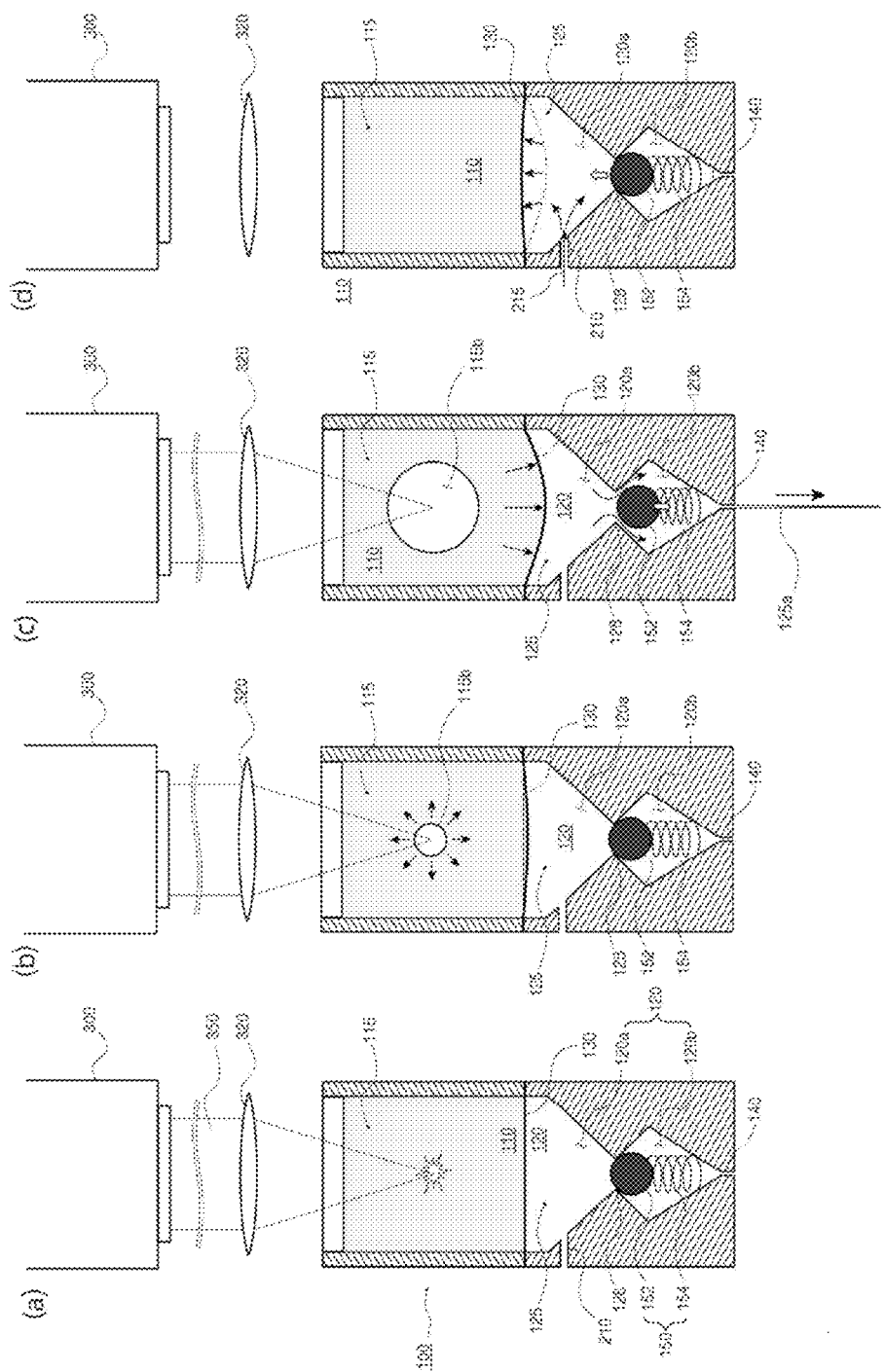
FIG. 3 is a view showing a detailed structure and an operation mechanism of a microjet drug injection device according to the present disclosure.

FIG. 1 is a diagram showing an overall configuration of a microjet drug injection device according to the present disclosure. FIG. 2 is a view showing a cross-sectional structure of the device shown in FIG. 1. FIG. 3 is a view showing a detailed structure and an operation mechanism of a microjet drug injection device according to the present disclosure.

Referring to FIG. 1, a microjet drug delivery device according to one embodiment of the present disclosure includes a microjet injector unit 100 configured to store a predetermined amount of a drug solution therein, and to inject the drug in a microjet form into a body, an energy-focusing unit 300 configured to supply propulsion energy for ejecting the drug from the microjet injector unit 100 in a microjet form; and a drug storage unit 200 configured to supply the drug to the microjet injector unit 100.

In the embodiment of FIG. 1, a laser unit 300 is used as the energy-focusing unit. In the embodiment in FIG. 1, in use thereof, the microjet injector unit 100 may be mounted to a distal end of a laser tip from which the laser beam is emitted from the laser unit 300. Particularly, the microjet drug injection device according to the present disclosure may be suitably applied to a skin treatment or cosmetic field. In this case, in use of the device, the microjet injector unit 100 may be simply attached to the therapeutic laser unit, which is commonly used in skin care facilities, without having to have a separate laser unit. Therefore, the device according to the present disclosure is very advantageous in terms of ease of use and usability.

As illustrated, the microjet injector unit 100 has an overall structure where two chambers are formed to be consecutive in one housing as shown in FIG. 2 and FIG. 3. A drug chamber 120 which stores a to-be-injected drug solution is disposed as a front portion of the microjet injector unit, and a pressure chamber 110 which is a pressure chamber for applying a driving force to the drug solution 125 of the drug chamber 120 and of which inner space is hermetically filled with a pressure driving liquid 105 is disposed as a rear portion of the microjet injector unit. The drug chamber and pressure chamber may fluid-communicate with each other.

As a partition wall which partitions the drug chamber 120 and the pressure chamber 110, an elastic membrane 130 is formed of an elastic material. The elastic membrane 130 is configured to be elastically expanded and deformed according to a change in a physical state (evaporation and, thus, overall volume increase) of the pressure driving liquid 110 in the pressure chamber 10 to apply pressure to the drug solution 200 in the adjacent drug chamber 20, so that the drug solution can be ejected.

In the microjet injector unit 100 according to the present disclosure, the driving force for ejecting the drug solution 125 in a microjet form is created from the pressure driving liquid 115 filled hermetically in the pressure chamber 110. According to the present disclosure, a vapor bubble 115b is rapidly generated in the hermetically filled pressure driving liquid 115. Thus, the elastic membrane 130 is momentarily strongly urged toward the drug chamber due to an increase in the total volume of the pressure driving liquid 115 due to the generation of the bubble. This allows the propulsion pressure to be applied to the to-be-ejected drug solution 125 within the drug chamber 120.

As shown in FIG. 3, when a strong energy (for example, a laser or an electric spark) is instantaneously concentrated on the pressure driving liquid 115 hermetically filled in the pressure chamber 110 according to the present disclosure, the pressure driving liquid 115 is vaporized, thereby creating a bubble 115b in the liquid. The vapor bubble 115b generated in the pressure driving liquid 115 expands instantaneously and then disappears when irradiation of the laser or the like is stopped. Due to the rapid expansion of the bubble 115b, the elastic membrane 130 is deformed to the outside, that is, toward the drug chamber (see FIG. 3c). This deformation of the elastic membrane 130 exerts an external force onto the drug solution 125 in the adjacent drug chamber 120. This allows the drug solution 125 to be ejected through a microjet nozzle 140 having a very small diameter in the form of a high-speed microjet sufficient to penetrate skin tissue.

Hereinafter, the components constituting the microjet drug delivery system according to the present disclosure as described above will be described in more detail with reference to the accompanying drawings.

With reference to FIG. 1 to FIG. 3 showing the microjet drug injection device according to the present disclosure, first, the microjet drug injection device according to the present disclosure includes the microjet injector unit 100 configured to store a predetermined amount of a drug solution therein, and to eject the microjet into the body to inject the drug into the body.

FIG. 3 is a view showing the structure and operation mechanism of the microjet injector unit 100 in more detail. As shown in FIG. 3, according to the present disclosure, the microjet injector unit 100 may include the pressure chamber 110 in which a pressure driving liquid 115 is hermetically filled; the drug chamber 120 fluidly-communicating with and adjacent to the pressure chamber 110 and containing a to-be-ejected drug solution therein; and the elastic membrane 130 arranged to partition the pressure chamber 110 and the drug chamber 120.

The pressure chamber 110 has an enclosed structure as a whole and has an accommodation space of a certain volume therein. In the interior space thereof, the pressure driving liquid 115 as a fluid for creating propulsion force is hermetically filled without voids therein.

According to the embodiment shown in FIGS. 1 to 3, the pressure chamber no may be formed in a substantially cylindrical cylinder shape. The top of the pressure chamber 110 may be made of a transparent material so that the laser beam can pass therethrough. The bottom of the chamber may be configured to be blocked by an elastic membrane 130.

As the pressure driving liquid 115 filling the inside of the pressure chamber 110, basically, ordinary water may be used. In addition to the water, various liquid materials such as polymers sol and gel, such as alcohol or polyethylene glycol, may also be used as the pressure driving liquid 115. Further, the pressure driving liquid 115 may preferably include a degassed liquid for minimizing the residual bubble in the generation of the bubble 115b.

Furthermore, the pressure driving liquid may be prepared by adding an electrolyte (such as salt) to pure water. In this case, since the molecules are ionized and, thus, the energy required for the collapse of the molecular structure of the liquid is small, the bubble may be formed with better efficiency.

The drug chamber 120 is adjacent to the chamber 110 under the pressure chamber 110. The drug solution 125 is stored in the inside of the drug chamber 120. A micro nozzle 140 having a fine diameter is formed in the lower end of the drug chamber 120. As described above, the drug solution 125 may be ejected in the form of a high-speed microjet through the micro nozzle 140 by a propulsion force by which the pressure driving liquid 115 in the pressure chamber 110 pushes the elastic membrane 130. The diameter of the micro nozzle 140 may be varied according to a desired ejection speed, a target ejection amount, and the like. The diameter may be, for example, in a range of 150 μm to 300 μm.

Further, according to the embodiment shown in FIG. 3, a first space 120a contacting the elastic membrane 130 and a second space 120b connecting the micro nozzle 140 are defined in the drug chamber 120. That is, the drug chamber 120 may be configured as dual chambers. This configuration may be a major feature which allows the microjet drug injection device according to the present disclosure to be distinct from conventional microjet drug injection devices.

Referring to FIG. 3, a boundary portion between the first space 120a and the second space 120b of the drug chamber 120 may be formed as a connection neck 128 having a concave narrowed shape. According to another major feature of the present disclosure, the connection neck 128 is provided with a nozzle closure 150 and the closure 150 is capable of opening or closing the connection neck 128.

According to the present disclosure, the nozzle closure 150 temporarily seals a space (in the embodiment shown in FIG. 3, the first space 120a) defined by at least the elastic membrane 130 among the inner spaces of the drug chamber 120, thereby deactivating the fluidly communicating state by blocking the external atmosphere from the sealed space.

The nozzle closure 150 is basically in an opening mode during creation of the bubble 115b in the pressure driving liquid 115 and during the ejection of the drug solution 125 out of the micro nozzle 140 by expansion of the elastic membrane 130. To the contrary, as the bubble 115b created in the pressure driving liquid 115 in the pressure chamber no disappears, and, thus, the internal pressure of the pressure chamber no is lowered due to recovery of the elastic membrane 130 to its original state, the closure 150 closes the connection neck 128 in a closing mode. Accordingly, the first space 120a partially defined by the elastic membrane 130 is fluidly blocked from the atmospheric pressure outside the micro nozzle 140.

According to the present disclosure, the nozzle closure 150 as described above may be implemented as a check valve. The check valve allows the drug solution 125 to move from the first space 120a to the second space 120b, but blocks the solution 125 from moving from the second space 120b to the first space 120a. In the embodiment shown in FIG. 3, the nozzle closure 150, implemented as the check valve, may comprise a bearing ball 152 and a support spring 154 for supporting the ball bearing 152. However, the present disclosure is not limited to this.

According to the embodiment shown in FIG. 3, the bearing ball 152 and the support spring 154 are disposed in the second space 120b of the drug chamber no. The bearing ball 152 has a diameter greater than the diameter of the connection neck 128 between the first space 120a and the second space 120b. Thereby, when the ball is brought into close contact with the connection neck 128, the neck may be completely closed by the ball. The support spring 154 may be embodied as a compression spring for resiliently supporting the bearing ball 152 in the direction of the connection neck 128. In this connection, the tension of the support spring 154 is basically configured such that the bearing ball 152 may be brought into close contact with the connection neck 128. The tension of the support spring 154 may be further configured such that when the drug solution passes through the connection neck 128 due to the pressure at the time of expanding the elastic membrane 130, a large resistance force resulting from the spring may not lead to the speed reduction of the drug ejection.

Figure 4:
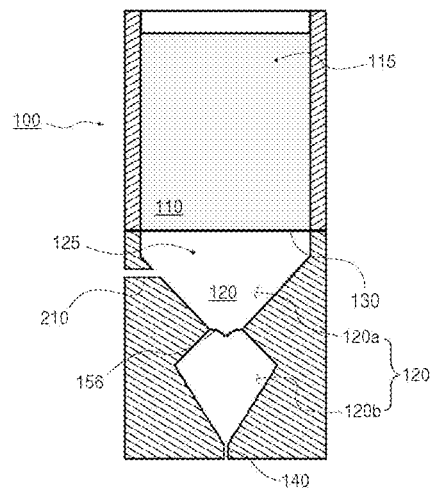
FIG. 4 shows another embodiment of a microjet injector unit in a microjet drug injection device according to the present disclosure.

Although, in the embodiment shown in FIG. 3, the nozzle closure 150 includes the bearing ball 152 and the support spring 154, but the present invention is not limited thereto. That is, in order to achieve the effect according to the present disclosure, the closure is not necessarily limited to the above-described form. For example, as shown in FIG. 4, the configuration of the nozzle closure 150 may include as a valve 156 such as the heart valve. Further, the support spring 154 may be replaced with another known equivalent elastic means configured to elastically support the bearing ball 152 in the direction of the connection neck 128. The bearing ball 152 is not necessarily limited to a spherical shape, as in the embodiment shown, but may be embodied in various forms without departing from its essential function. For example, the ball bearing may be embodied in a hemispherical shape or a disk shape.

Figure 5:
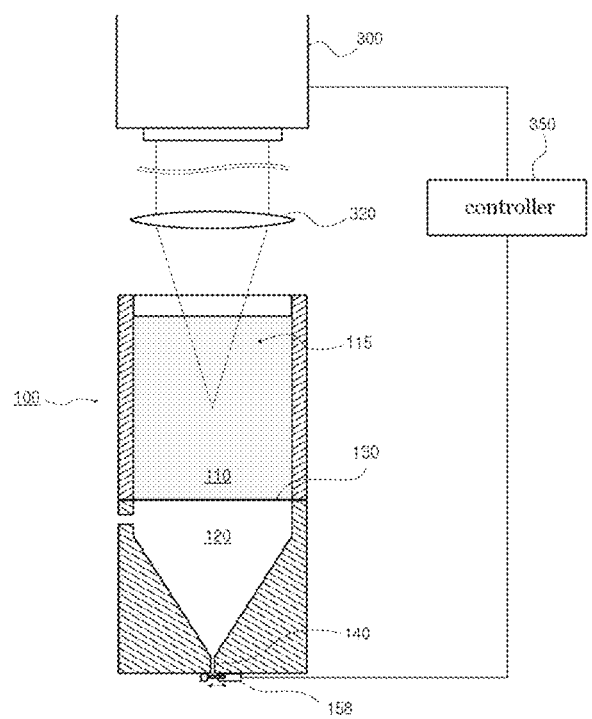
FIG. 5 shows still another embodiment of a microjet injector unit in a microjet drug injection device according to the present disclosure.

Further, according to the embodiment shown in FIGS. 3 and 4, the nozzle closure 150 is disposed in the interior of the drug chamber 120 and operates automatically according to the flow of the drug solution, so that no separate technical means for opening and closing the nozzle closure 150 is required. However, the present invention is not necessarily limited to such a configuration. For example, as in the embodiment shown in FIG. 5, it is also possible to place the nozzle closure outside of the drug chamber 120 in the form of a shutter 158 that directly opens and closes the micro nozzle 140. In this case, the shutter 158 should be operated so that the timing of the opening and closing thereof is precisely synchronized with the driving timing of the laser unit 300. Therefore, in order to synchronize the shutter and the laser unit, a separate controller 350 may be additionally provided.

According to the drug delivery device according to the present disclosure, as shown in FIG. 1, the drug storage unit 200 storing a to-be-reinjected drug may be provided. The drug solution 215 stored in the drug storage unit 200 is supplied to the inside of the drug chamber 120 through a drug supply channel 250 connected to one side of the drug chamber 120.

According to the illustrated embodiment, the drug storage unit 200 may include an ample cylinder 210 having a constant internal volume and a piston 220 slidably moving within the ample cylinder 210, as in the embodiment shown in FIG. 2. As will be described later, according to the present disclosure, the drug supply from the drug storage unit 200 to the drug chamber 120 may be automatically performed in the microjet ejection process, without the need for an injection means such as a pump. As shown in FIG. 2, the drug storage unit 200 has a configuration similar to a simple syringe composed of only the ample cylinder 210 and the piston 220.

In the case of the embodiment of the drug storage unit 200 shown in FIG. 2, the drug solution 215 in the drug storage unit 200 is supplied to the first space 120a of the drug chamber via the following mechanism. First, the elastic membrane 130 is expanded and returned to its original position due to generation/disappearance of the bubble 115b in the pressure chamber 110. As a result, the pressure inside the first space 120a fluctuates (decreases). Due to the pressure difference between the drug storage unit 200 and the drug chamber 120, the drug solution 215 may be sucked and moved from the drug storage unit 200 to the drug chamber 120.

Thus, according to the embodiment shown in FIG. 2, the drug solution 215 may be automatically moved via the variation of the internal pressure of the drug chamber 120 caused solely by the operation of the microjet injector unit 100, without additional driving means such as a separate micro pump. Further, the same amount of drug as the drug ejected in the form of a microjet is supplemented, and, thus, the internal pressure in the drug chamber 120 and the drug amount therein is immediately recovered to the pressure and amount before the ejection, thereby preventing the inflow of air from the outside, and, at the same time, enabling continuous re-injections.

The drug supply channel 250 connecting the drug chamber 120 and the drug storage unit 200 may be connected to a side face of the first space 120a defined by the elastic membrane 130 and may be more advantageously disposed adjacent to the elastic membrane 130. This allows the drug to be supplied directly to the point of creation of the back-pressure as the elastic membrane 130 retracts. Further, the drug supply channel 250 is not limited to one channel as shown in FIG. 3, and two or more drug supply channels 250 may be formed. Further, when a plurality of drug supply channels 250 are formed, it may be preferable that the plurality of channels 250 are disposed at equal intervals, and, thus, the pressure distribution may be made uniform.

Next, the elastic membrane 130 may be embodied as a thin film having elastic restoring force, and may be disposed between the pressure chamber no and the drug chamber 120 to form a boundary therebetween. That is, the pressure chamber 110 and the drug chamber 120 are separated from each other via the elastic membrane 130, and, at the same time, at least one of the pressure chamber 110 and the drug chamber 120 is brought into contact with the elastic membrane 130. Accordingly, when the volume of the pressure driving liquid 115 in the pressure chamber 110 expands due to the creation of the bubble 115b, the deformation of the elastic membrane 130 may apply pressure to the drug solution 125 in the drug chamber 120.

The elastic membrane 130 may be made of a thin rubber material, preferably a silicone rubber. The silicone rubber not only has excellent stretchability but also has a low thermal conductivity, thereby effectively shielding the heat generated by the laser irradiation and preventing the deterioration and corruption of the drug due to heat transfer. Alternatively, the material of the elastic membrane 130 may employ any material having elasticity and liquid impermeability, depending on the choice of a person skilled in the art. An example of such a material may be nitrile butadiene rubber (NBR).

Next, the laser unit 300 concentrates the laser light (energy) on the pressure driving liquid 115 in the pressure chamber 110 to create a bubble 115b therein. The laser unit constitutes the energy-focusing unit according to the present disclosure. In this embodiment, the laser unit 300 is illustrated as the energy-focusing unit, but the present invention is not necessarily limited thereto. For example, the energy focusing unit may employ an electric electrode configured to apply electric energy.

As the light source of the laser unit 300, any type of laser may be used. For example, various types of laser sources as known in the art, such as Er: YAG laser (wavelength 2.94 μm), Nd: YAG laser (wavelength 1.06 μm), ruby laser, alexandrite laser, Nd: Glass laser, Er: Glass fiber laser may be employed. In particular, the Er: YAG lasers produce the most absorbable wavelength into water. Thus, when water is used as the pressure driving liquid, the Er: YAG laser may be used suitably for the present disclosure, since bubble generation and expansion may occur well.

Further, as shown in FIG. 3, the laser may be injected such that the laser light emitted from the laser unit 300 is focused, through a condenser lens 320, toward a point within the pressure driving liquid 115 in the pressure chamber 120. In this case, a portion of a wall (e.g., an upper wall) of the pressure chamber no should be formed of a transparent member so that laser light may be transmitted therethrough. In this connection, for example, when the Nd: YAG laser is used as a light emitting source of the laser unit, the transparent member may include a BK7 glass which may not be affected by repetitive liquid volume fluctuations and heat changes. When the Er: YAG laser is used as the light emitting source of the laser unit 300, a sapphire window may be used as the transparent member. Other materials and members such as other types of glasses or transparent acrylic members may be used as the transparent member.

Hereinafter, with reference to FIG. 3, a basic operation principle, a concrete operation, and a corresponding operation effect of the microjet drug injection device according to the present disclosure will be described in detail.

First, regarding the basic operation principle of the microjet drug injection device according to the present disclosure, the microjet drug injection device according to the present disclosure basically blocks external air from entering the first space defined by the elastic membrane before the drug is re-ejected after initial ejection thereof, which may otherwise cause ejection pressure reduction of the drug. This will prevent ejection speed and penetration performance degradation. As described above, the bubble formation resulting from the external air which may adversely affect the ejection pressure may be caused by the back-pressure generated in the drug chamber in the process of the elastic membrane retracting after the initial microjet ejection. As described above, according to a preferred aspect according to the present disclosure, prior to re-ejection after the initial microjet ejection, the same amount of drug as the initially ejected drug may be automatically charged into the drug chamber, thereby maintaining the internal pressure therein. This may prevent the introduction of external air into the drug chamber that may otherwise cause a significant reduction in the propulsion force of the drug microjet.

The specific operations of the microjet drug injection device according to the present disclosure having the above-described technical feature will be described step by step with reference to FIG. 3 attached herein.

First, the laser unit 300 is driven to create a bubble 115b in the pressure driving liquid 115 in the pressure chamber 110. In the embodiment shown, a handheld laser unit 300 using the Er: YAG laser was used as a laser source with a wavelength of 2940 nm and a pulse width of 150-200 μs. Referring to FIG. 3A, the laser beam 310 emitted via the operation of the laser unit 300 is irradiated into the interior of the drug chamber 110 through the condenser lens 320.

The pressure driving liquid 115 containing water as a main component is filled in the pressure chamber no of the microjet injector unit 100. Water as the pressure driving liquid 115 has the property of absorbing light having a wavelength of 2900 nm most effectively. As the irradiated laser beam 350 is absorbed into the pressure driving liquid 115, the pressure driving liquid 115 changes from a liquid state to a gas state around a laser focus point on which energy is concentrated. Accordingly, a vapor bubble 115b is created inside the pressure driving liquid 115 as shown in FIG. 3b.

The vapor bubble 115b created in the pressure driving liquid 115 rapidly expands and has increased volume. Accordingly, the pressure of the entire pressure chamber 120 is increased. This results in the expansion of the elastic membrane 130 located below the pressure chamber 120 (see FIG. 3c).

As the internal pressure of the pressure chamber 120 increases and thus the elastic membrane 130 expands, the propulsion pressure is transferred to the drug solution 125 in the drug chamber 120 adjacent to the membrane. The drug solution 125 in the first space 120a, upon receiving direct pressure from the elastic membrane 130, is strongly pushed toward the bearing ball 152. The bearing ball 152 is resiliently pushed by the pressure of the drug solution. Thus, the connection neck 128 in the drug chamber 120 is opened. Thus, as shown in FIG. 3c, the drug solution 125 is rapidly moved from the first space 120a of the drug chamber 120 to the second space 120b thereof.

The propulsion pressure and kinetic energy are transferred to the drug solution in the second space 120b of the drug chamber 120 by the movement flow of the drug solution 125 and urged movement of the bearing ball 152. Thus, the drug solution 125 is ejected through the micro nozzle 140 in the form of a microjet 125a.

Then, as shown in FIG. 3d, when the operation of the laser unit 300 is stopped, the vapor bubble 115b created in the pressure driving liquid 115 of the pressure chamber 110 rapidly shrinks and disappears. Accordingly, the volume of the pressure driving liquid 115 is restored to its original volume, and, thus, the elastic membrane 130 is also restored to its original state while being expanded. As a result, as the elastic membrane 130 returns to its original state, the pressure applied to the bearing ball 152 decreases. Accordingly, the bearing ball 152 moves upward again by the compressive force of the support spring 154, and, thus, the ball is in close contact with the connection neck 128. Thus, the movement of the drug solution 125 from the first space 120a to the second space 120b is blocked.

As the bearing ball 152 closes the connection neck 128, the first space 120a of the drug chamber 120 is fluidly shut off from the atmosphere outside the micro nozzle 140. Therefore, even when the internal pressure of the first space 120a falls below the external atmospheric pressure as the elastic membrane 130 continuously recovers and returns to the original position, air from the atmosphere outside the micro nozzle 140 is prevented from flowing into the first space 120a.

Meanwhile, the amount of the drug solution is reduced by the amount of ejected drug in the first space 120a of the drug chamber 120 by microjet ejection. Thus, when the bearing ball 152 closes the connection neck 128 and the elastic membrane 130 is continuously retracted from the extended state to the original state, the internal pressure of the first space 120a is reduced. In this connection, in the case of the conventional microjet drug injection devices, because there is no configuration of the nozzle closure 150, which is a key feature of the present disclosure, when the elastic membrane 130 is restored to its original state, the pressure inside the drug chamber is lower than the external atmospheric pressure. Thus, there is a problem that air is introduced into the drug chamber from the outside by back-pressure. However, according to the present disclosure, due to the action of the nozzle closure 150, the problem of inflow of external air into the chamber after such ejection may be effectively prevented.

As shown in FIG. 2 and FIG. 3, according to a preferred aspect of the present disclosure, the first space 200a of the drug chamber 120 and the drug storage unit 200 exposed to the external atmospheric pressure are fluid-connected through the drug supply channel 250. As described above, after the microjet ejection, the inner pressure of the first space 120a is lowered by the retraction of the elastic membrane 130 to be lower than the atmospheric pressure. Thus, as shown in FIG. 3d, the drug solution 215 stored in the drug storage unit 200 is sucked into the first space 120a of the drug chamber 120 having a relatively low inner pressure by a pressure difference between the first space and the inner space of the storage unit. At the same time, the piston 220 of the drug storage unit 200 is subjected to atmospheric pressure to overcome frictional forces and then move toward the drug chamber 120 within the ample cylinder 210 by a predetermined distance each ejection time.

Figure 8:
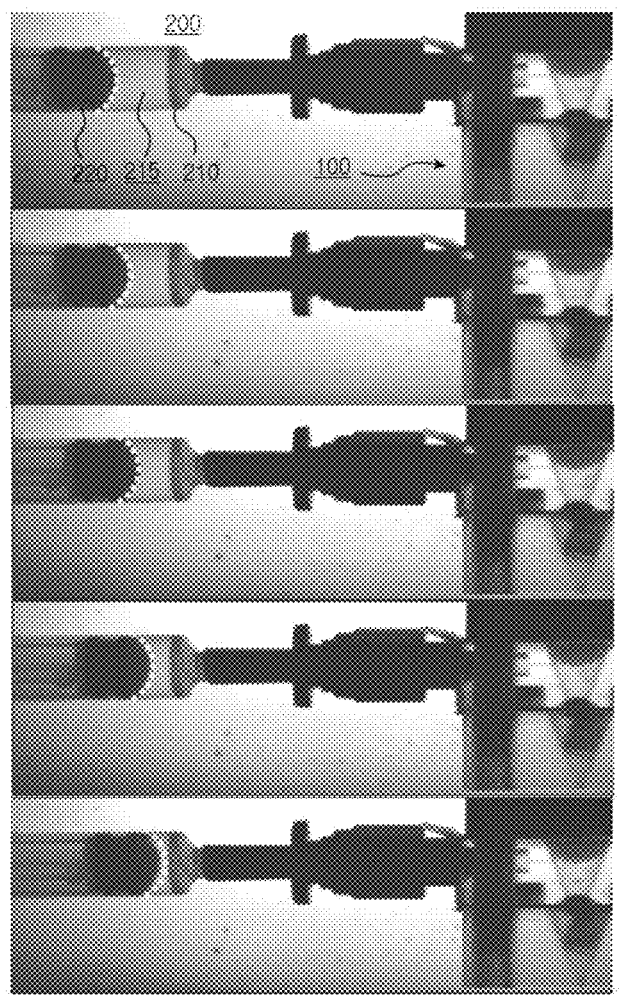
FIG. 8 is a photograph continuously photographing a piston movement in a drug storage unit in the drug injection device according to the present disclosure.

FIG. 8 is a photograph continuously photographing, at an interval of 2 seconds, a piston movement in a drug storage unit in the drug injection device according to the present disclosure. As shown in FIG. 8, it may be confirmed that in the microjet drug injection device according to the present disclosure, a separate injection means such as a pump is not required for replenishment of the drug 215, but, rather, the drug recharge may be automatically activated solely based on the operation of the microjet injector unit 100.

In the case of the embodiment shown in FIG. 8, the piston 220 moved about 0.5 mm per a single microjet ejection. The inner diameter of the ample cylinder 210 was 5 mm. Thus, it may be seen that the drug was charged about 40 uL per a single laser oscillation.

In order to confirm the performance and the improved effect of the microjet drug injection device according to the present disclosure as described above, a test device according to the present disclosure was fabricated. Then, a comparison test was conducted between the test device and the conventional microjet drug injection device. Hereinafter, the above-described comparison test results will be described with reference to the accompanying drawings.

Figure 6:
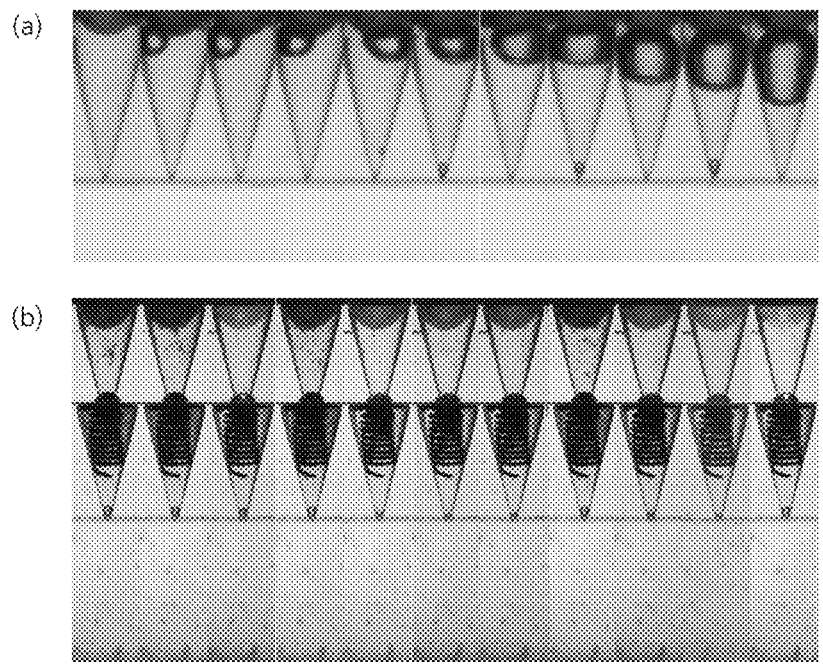
FIG. 6 is a comparative photograph showing continuous images of air bubble formations in a drug chamber over repetitive ejections for a conventional microjet drug injection device and for a drug injection device according to the present disclosure.
Figure 7:
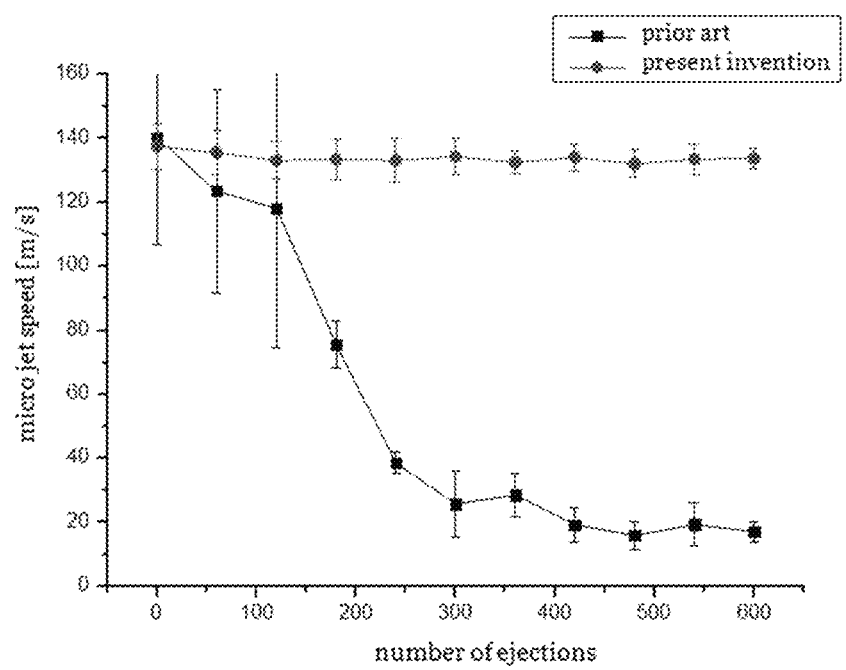
FIG. 7 is a comparative graph showing a change in microjet speed based on the number of ejections during continuous ejections for a conventional microjet drug injection device and for a drug injection device according to the present disclosure.

FIG. 6 is a comparative photograph showing continuous images of air bubble formations in a drug chamber over repetitive ejections for a conventional microjet drug injection device and for a drug injection device according to the present disclosure. FIG. 7 is a comparative graph showing a change in microjet speed based on the number of ejections during continuous ejections for a conventional microjet drug injection device and for a drug injection device according to the present disclosure.

The laser unit used in the comparative test is a medical handheld laser unit 300 using an Er: YAG laser as a laser source with a wavelength of 2940 nm and a pulse width of 150-200 µs. In this regard, the nozzle diameter of the microjet injector unit was 300 µm. Further, the laser operation was configured to have an ejection rate of 10 times per second for each of the conventional device and the present test device. In FIGS. 6 and 7, the photographing and speed measurement of the devices shows results for continuous ejections (total 600 ejections) for 60 seconds at an interval of 6 seconds (10 ejections per second) for each of the prior art and present devices.

FIG. 6a shows photographs of continuous growths of air bubbles in the drug chamber in the conventional microjet drug injection device which does not include the characteristic configuration according to the present disclosure. Referring to FIG. 6a, in the case of the conventional microjet drug injection device, the air bubble creation in the drug chamber started to be clearly confirmed after about 6 seconds (60 ejections) after the start of ejection. In this connection, it is confirmed that the air bubble grows gradually as the number of ejections increases, such that the bubbles completely cover the surface of the elastic membrane.

To the contrary, in the case of the drug injection device according to the present disclosure, air bubbles were not created in the drug chamber even though the number of ejections increased, as shown in FIG. 6b. From the above photographed results, it was confirmed that the microjet drug injection device according to the present disclosure has an effect of suppressing air bubble creation in the drug chamber.

Further, referring to FIG. 7 showing the microjet speed change based on the number of ejections, in the case of the conventional microjet drug injection device which does not include the features according to the present disclosure, as the number of ejection times increases, the microjet ejection speed is significantly reduced.

In particular, according to the result graph of FIG. 7, as for the conventional microjet drug injection device, the initial microjet ejection speed was 140 m/s. Then, since approximately 150 ejections have been performed, the microjet ejection speed has begun to decrease. At 200 ejection times, the microjet ejection speed decreased to about 60 m/s. Subsequently, after 400 ejections, the speed dropped below 20 m/s. Therefore, it was confirmed that microjet ejection was not practically performed.

To the contrary, in the case of the drug injection device according to the present disclosure, as shown in FIG. 6b, the initial microjet ejection speed was measured at about 135 m/s. Even with increasing number of ejections, the initial microjet ejection speed did not vary significantly, and, thus, almost the same microjet ejection speed was maintained.

Figure 9:
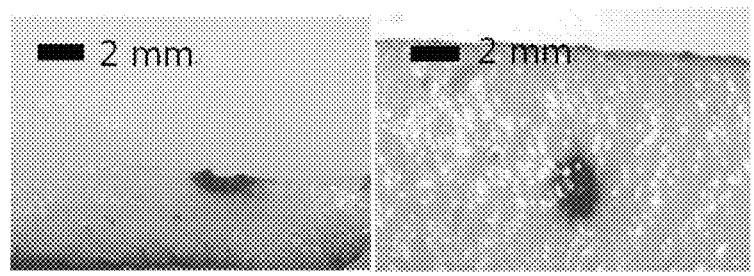
FIG. 9 is a photograph showing a test result of injecting a drug into pig skin to confirm the penetration performance of the drug injection device according to the present disclosure.
Figure 10:
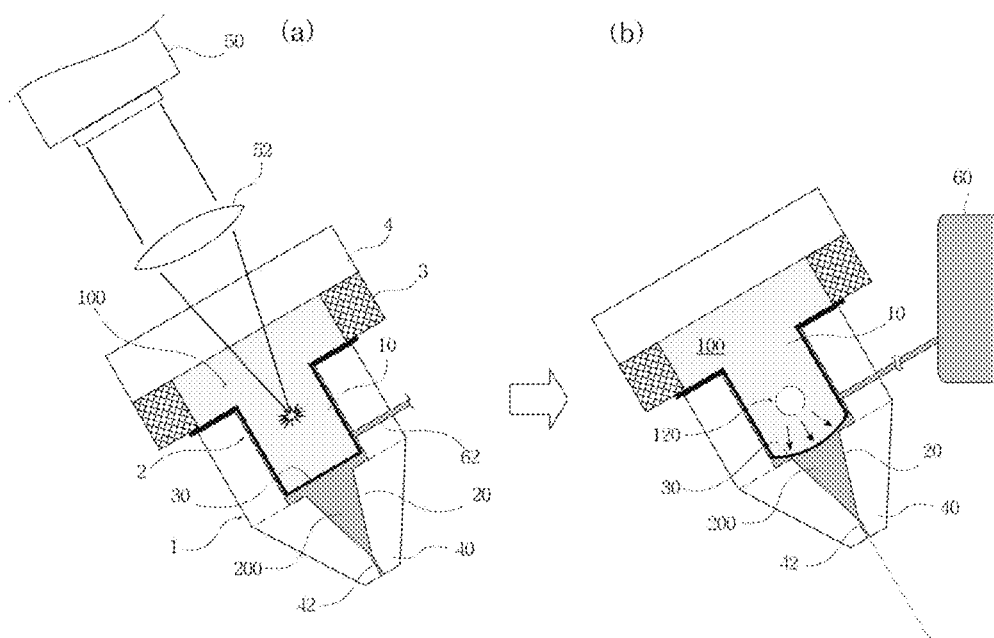
FIG. 10 is a view illustrating the structure and operation of the prior art laser-bubble based microjet drug delivery device.

FIG. 9 is a photograph showing a test result of injecting a drug into pig skin to confirm the penetration performance of the drug injection device according to the present disclosure.

Table 1 below shows measurements of microjet ejection speed and penetration performance of the drug injection device according to the present disclosure. The drug injection device used in FIG. 9 and Table 1 used the same unit as the laser unit used in the above-mentioned test, and the micro nozzle diameter was 300 μm.

TABLE 1

| Factors | Performance |
| --- | --- |
| Ejection speed (m/s) | 133.92 |
| penetration depth (μm) | 667 |
| penetration diameter (mm) | 2.0 |

Penetration performance of drug injection device according to the present disclosure As seen from FIG. 9 and the results of Table 1 above, it may be confirmed that the microjet drug injection device according to the present disclosure exhibits the followings from the test results on pig skin. Overall good penetration patterns and values are measured. In particular, the penetration depth was sufficient to allow the drug microjet to sufficiently penetrate into between the epidermis and the dermis (500 to 1000 μm), even with the output of a typical medical laser unit. Thus, the present device may be effectively used as a drug injection device for living tissue.

Therefore, according to the present disclosure microjet drug injection device, various medical drugs such as therapeutic drugs, anesthetics, hormones, vaccines, and various kinds of drugs such as cosmetic lotion, tattoo liquid and botulinum toxin (aka Botox) may be injected into human or animal body without pain such that the ejection amount may be accurately adjusted and correct dose may be administered in a repeated manner. Thus, the present device may be particularly advantageously used in various industrial fields such as the medical field, the cosmetic field, the tattoo field, and the livestock field.

On the other hand, in the explanation of the present disclosure, the term "drug" or "drug solution" has been used for illustrative purposes. The drug solution is not limited to a solution injected into a living tissue. Rather, drug solution may conceptually encompass liquid injections such as foods (bread, confectionery, jelly, etc.), soft synthetic resin, dyes and additives added to fibers, etc.

What is claimed is:

1. A microjet drug injection device comprising:
 a pressure chamber having a sealed inner space defined therein, wherein a pressure driving liquid is hermetically filled in the pressure chamber;
 a drug chamber having a drug solution contained therein, wherein the drug chamber has a micro nozzle defined in a wall thereof for discharging the drug solution out of the drug chamber;
 an elastic membrane configured to be elastically expandable and restorable and to separate the pressure chamber and the drug chamber from each other;
 an energy-focusing unit configured to concentrates energy on the pressure driving liquid in the pressure chamber to create a bubble in the pressure chamber;
 a drug storage unit being in fluid communication with the drug chamber through a drug supply channel, wherein the drug storage unit contains a drug solution stored therein, and the storage unit is configured to supply the drug solution into the drug chamber through the drug supply channel, wherein the drug chamber has a partial inner space defined therein, wherein the partial inner space is in fluid communication with the drug supply channel and is partially defined by the membrane; and
 a nozzle closure disposed inside or outside the drug chamber, wherein the nozzle closure is configured to block inflow of air outside the micro-nozzle into the partial inner space after the elastic membrane has expanded and before elastic recovery of the membrane is completed.

2. The device of claim 1, wherein the nozzle closure is disposed inside the drug chamber, wherein the drug chamber is partitioned into a first inner space and a second inner space by an intermediate wall, and the first space and the second space are in fluid communication through an opening defined in the intermediate wall, wherein the nozzle is defined in the wall defining the second space, wherein the partial inner space corresponds to the first space.

3. The device of claim 2, wherein the nozzle closure includes a check valve, wherein the check valve is configured to allow movement of the drug solution from the first space to the second space, but to block movement of the drug solution from the second space to the first space.

4. The device of claim 3, wherein the nozzle closure includes:
 a bearing ball having a diameter greater than the opening; and
 a support spring configured for elastically supporting the bearing ball such that the bearing ball closes the opening.

5. The device of claim 2, wherein when an inner pressure of the first space drops due to ejection of the drug solution from the first space out of the drug chamber, the drug solution is sucked from the storage unit into the first space by a pressure difference between the first space and an inner space of the storage unit.

6. The device of claim 1, wherein the energy-focusing unit includes a laser unit configured to irradiate a laser beam to the pressure driving liquid in the pressure chamber.

7. The device of claim 6, wherein the laser beam emitted from the laser unit is focused at one point in the pressure driving liquid.

8. The device of claim 6, wherein the laser unit include an Er:YAG laser unit.

9. A microjet drug injection device comprising:
 a pressure chamber having a sealed inner space defined therein, wherein a pressure driving liquid is hermetically filled in the pressure chamber;
 a drug chamber having a drug solution contained therein, wherein the drug chamber has a micro nozzle defined in a wall thereof for discharging the drug solution out of the drug chamber, wherein the drug chamber fluid-communicates with an external drug supply channel, wherein the drug chamber is partitioned into a first inner space and a second inner space by an intermediate wall, and the first space and the second space are in fluid communication through an opening defined in the intermediate wall, wherein the nozzle is defined in the wall defining the second space, wherein the drug supply channel fluid-communicates with the first space;

an elastic membrane configured to be elastically expandable and restorable and to separate the pressure chamber and the drug chamber from each other, wherein the first space is partially defined by the membrane;

an energy-focusing unit configured to concentrates energy on the pressure driving liquid in the pressure chamber to create a bubble in the pressure chamber; and a nozzle closure disposed in the second space, wherein the nozzle closure includes a check valve, wherein the check valve is configured to allow movement of the drug solution from the first space through the opening to the second space, but to block movement of the drug solution from the second space to the first space.

10. The device of claim 9, wherein the nozzle closure includes:
a bearing ball having a diameter greater than the opening; and
a support spring configured for elastically supporting the bearing ball such that the bearing ball closes the opening.

11. A microjet drug injection device, wherein the device is removably mounted to a laser tip of a laser unit to emit a laser beam, wherein the device comprises:
a pressure chamber having a sealed inner space defined therein, wherein a pressure driving liquid is hermetically filled in the pressure chamber, wherein when the laser unit is mounted to the laser tip and the laser beam is irradiated into the pressure driving liquid in the pressure chamber to create a bubble in the pressure chamber;
a drug chamber having a drug solution contained therein, wherein the drug chamber has a micro nozzle defined in a wall thereof for discharging the drug solution out of the drug chamber;
an elastic membrane configured to be elastically expandable and restorable and to separate the pressure chamber and the drug chamber from each other;
a drug storage unit being in fluid communication with the drug chamber through a drug supply channel, wherein the drug storage unit contains a drug solution stored therein, and the storage unit is configured to supply the drug solution into the drug chamber through the drug supply channel, wherein the drug chamber has a partial inner space defined therein, wherein the partial inner space is in fluid communication with the drug supply channel and is partially defined by the membrane; and
a nozzle closure disposed inside or outside the drug chamber, wherein the nozzle closure is configured to block inflow of air outside the micro-nozzle into the partial inner space after the elastic membrane has expanded and before elastic recovery of the membrane is completed.

12. The device of claim 11, wherein the nozzle closure is disposed inside the drug chamber, wherein the drug chamber is partitioned into a first inner space and a second inner space by an intermediate wall, and the first space and the second space are in fluid communication through an opening defined in the intermediate wall, wherein the nozzle is defined in the wall defining the second space, wherein the partial inner space corresponds to the first space.

13. The device of claim 12, wherein the nozzle closure includes a check valve, wherein the check valve is configured to allow movement of the drug solution from the first space to the second space, but to block movement of the drug solution from the second space to the first space.

14. The device of claim 13, wherein the nozzle closure includes:
a bearing ball having a diameter greater than the opening; and
a support spring configured for elastically supporting the bearing ball such that the bearing ball closes the opening.

15. The device of claim 1, wherein the drug storage unit further comprises an ample cylinder having a constant volume and a piston slidably moving within the ample cylinder.

16. The device of claim 1, wherein a microjet injection speed has less than 14% variation during the initial 200 cycles.

* * * * *